United States Patent [19]
Sporer

[11] Patent Number: 5,387,231
[45] Date of Patent: Feb. 7, 1995

[54] ELECTROTHERAPY METHOD

[76] Inventor: Patsy Sporer, Box 90, Heufner Rd., Marble, Pa. 16334

[21] Appl. No.: 253,616

[22] Filed: Jun. 3, 1994

Related U.S. Application Data

[63] Continuation of Ser. No. 918,831, Jul. 21, 1992, abandoned.

[51] Int. Cl.$^6$ .............................................. A61N 1/36
[52] U.S. Cl. ................................... 607/48; 607/70
[58] Field of Search .................. 607/48, 50, 66, 70, 607/71, 74

[56] References Cited

U.S. PATENT DOCUMENTS

| | | | |
|---|---|---|---|
| 1,004,751 | 6/1935 | Fischer et al. | 607/66 |
| 1,155,036 | 9/1915 | Brooks et al. | 607/61 |
| 1,908,688 | 5/1933 | Call | 607/66 |
| 2,327,874 | 8/1943 | DeJong | 607/145 |
| 3,294,092 | 12/1960 | Landauer | 607/71 |
| 3,835,833 | 9/1974 | Limoge | 600/26 |
| 3,885,573 | 5/1975 | Hara | 607/68 |
| 3,888,261 | 6/1975 | Maurer | 607/61 |
| 3,908,669 | 9/1975 | Mau et al. | 607/74 |
| 3,955,583 | 5/1976 | Horauf | 607/47 |
| 4,106,513 | 8/1978 | Tzeng | 607/66 |
| 4,180,079 | 12/1979 | Wing | 607/69 |
| 4,646,744 | 3/1987 | Capel | 607/58 |
| 4,724,841 | 2/1988 | Kastrubin et al. | 607/45 |

FOREIGN PATENT DOCUMENTS

| | | | |
|---|---|---|---|
| 496878 | 1/1976 | Australia | 607/68 |
| 316994 | 11/1988 | European Pat. Off. | 607/61 |
| 367388 | 10/1989 | European Pat. Off. | 607/70 |
| 7442442 | 12/1974 | France | 607/68 |
| 2424033 | 4/1978 | France | 607/68 |
| 2023716 | 5/1970 | Germany | 607/68 |
| 2736345 | 8/1977 | Germany | 607/61 |
| 577323 | 7/1976 | Switzerland | 607/61 |

OTHER PUBLICATIONS

Hookea?-M. Patterson, 1986 pp. 130-131, 134-135.
The Body Electric-R. Becker & G. Selden 1985, pp. 223-225.
Cross Currents-R. O. Becker, MD.
L. A. Wallace-M.E.N.S. Therapy 1988 pp. 4-3, 5-1, 5-2, 5-3, 5-4, Case 1 pp. 2, 14-3, 14-8, 1st p. 0-1.
Modern Bioelectrically-A. A. Marino, 1988 pp. 163-168, pp. 497-516.

Primary Examiner—George Manuel
Attorney, Agent, or Firm—J. Stewart Brams

[57] ABSTRACT

A method of microcurrent electrotherapy utilizing a combination of specified values for selected parameters including electrical stimulus wave form, direction, magnitude, voltage, polarity and frequency to provide a variety of therapeutic enhancements.

26 Claims, 3 Drawing Sheets

ELECTROTHERAPY METHOD

This is a continuation-in-part of co-pending application Ser. No. 07/918,831 filed on Jul. 21, 1992, now abandoned.

BACKGROUND OF THE INVENTION

The present invention concerns methods of microcurrent electrotherapy for the relief or attenuation of pain through operative mechanisms including relaxation of involuntarily contracted muscles.

The art is replete with examples of electrotherapy methods and apparatus, known by a variety of names often depending upon the specific nature of the treatment regimen involved. Known designations include MCT (microcurrent therapy), NET (neuroelectrical therapy), MENS (minimal electrical non-invasive stimulation), and TENS (transcutaneous electrical stimulation).

Prior art examples from the wide variety of electrotherapy references include U. S. Pat. Nos. 4,646,744 (A Method of Applying an Electrical Signal Transcranially), 4,180,079 (An Electroacupuncture Instrument), and a number of documents relating generally to other aspects of electrotherapy methods and apparatus, including EPO applications 316,994 and 367,338, German patents 2,023,716 and 2,736,345, Swiss patent 577,323, French patent 242,033 and U.S. Pat. Nos. 3,294,092, 1,155,036, 1,908,688, 2,004,751 and 2,327,874. U.S. Pat. No. 3,885,573 discloses a therapeutical apparatus for applying the superposed output of DC and AC voltages. Australian patent 496878 and French patent 2295763 appear to be the respective Australian and French counterparts of above-cited U.S. Pat. No. 3,885,573.

Still other patent art relating to electrotherapy and variations includes U.S. Pat. Nos. 3,955,583, 4,724,841, 3,888,261 and 3,835,833, and German patent 2806569.

The literature of electrotherapy is also voluminous. Examples include: (1) Guidebook for Musculoskeletal Disfunctions by Donald Stragier, Micro-Med Systems, (describes the application of AC electrical stimulus to muscle origin and insertion points); (2) MENS Therapy Clinical Perspectives by Lynn A. Wallace; (3) Modern Bioelectricity, edited by Andrew A. Marino; (4) Hooked?—NET; The New Approach to Drug Cure by Meg Patterson; (5) The Body Electric—Electromagnetism and the Foundation of Life by Robert O. Becker, MD and Gary Selden; and (6) Cross Currents by Robert O. Becker, MD.

As noted, it is known in the prior art to superpose alternating current and direct current for electrotherapy treatment; however, a number of other properties of the electrical stimulus to be used, including polarity, voltage magnitude, current magnitude, and frequency can have a significant or even a determining impact upon the efficacy of the treatment. In addition, the direction of current flow through the muscle tissue is believed to be an important factor in the efficacy of the treatment.

The prior art has not contemplated the proper, effective combination of electrical parameters for truly effective electrotherapy. Prior art apparatus generally has operated at very high voltages or very high currents, both of which can have a diathermy effect on the tissue being treated. In many cases, the prior art may mention one or another of the various electrical parameters, but fails to consider the importance of other parameters. For example, known AC electrotherapy devices often provide such high currents that they bombard the tissue, or provide such low voltage that the electrical signal does not penetrate the skin.

Electrotherapy can be enormously beneficial in pain management. Many people go about their day-to-day lives afflicted with chronic pain conditions of various sorts, often having been told nothing can be done and that they simply must learn to live with the pain. The individual may experience chronic pain at any level of intensity from a minor nuisance to a thoroughly debilitating condition; however, for any level of chronic pain, the inescapable effect is going to be unnecessary limitations on the range of patient cognitive function in day-to-day living. Effective pain management thus is an important component of individual health care that can improve the patient's range and quality of cognitive function, and his or her overall quality of life. To the extent that these beneficial prospects can arise, the level of day-to-day stress imposed on those persons chronically afflicted with pain can be reduced.

In addition, an improved and more effective microcurrent therapy can offer the prospect of greater cost effectiveness in the treatment and management of pain, with the attendant benefits of wider patient participation, improved medical resource allocation, and the additional benefit to research of faster accumulation of larger volumes of patient treatment and response data.

BRIEF SUMMARY OF THE INVENTION

I have invented a novel and improved method of electrotherapy for pain treatment which takes account of a variety of electrical parameters, selection of appropriate values which provides electrotherapy that is both effective and economical in terms of the overall improvement that can be achieved in the patient's pain condition. My method contemplates superimposed AC and DC signals, predominately negative in polarity and preferably in low voltage, low current and low frequency ranges. My method also contemplates generally uniform direction of current flow through the muscle tissue from insertion to origin. Insertion and origin are references to the end attachment points of the muscle and refer, respectively, to the muscle attachments at the member that is generally regarded as being movable and the member that is generally regarded as stationary.

It is therefore one object of the invention to provide a novel and improved method of electrotherapy.

A further object of the invention is to provide a method of electrotherapy utilizing specified ranges of low voltage, current and frequency, and a uniform polarity in an electrical stimulus comprised of superposed AC and DC outputs.

These and other objects and further advantages of the invention will be more fully appreciated upon consideration of the following detailed description and the accompanying drawings, in which:

FIG. 1 is a schematic illustration of the application of my novel method according to one presently preferred embodiment thereof, and specifically as applied to the right biceps brachii muscle of the human anatomy;

FIG. 2 graphically illustrates an electrical stimulus voltage, polarity and wave form according to one preferred embodiment of my method;

DESCRIPTION OF THE PREFERRED EMBODIMENTS

Figure 1:
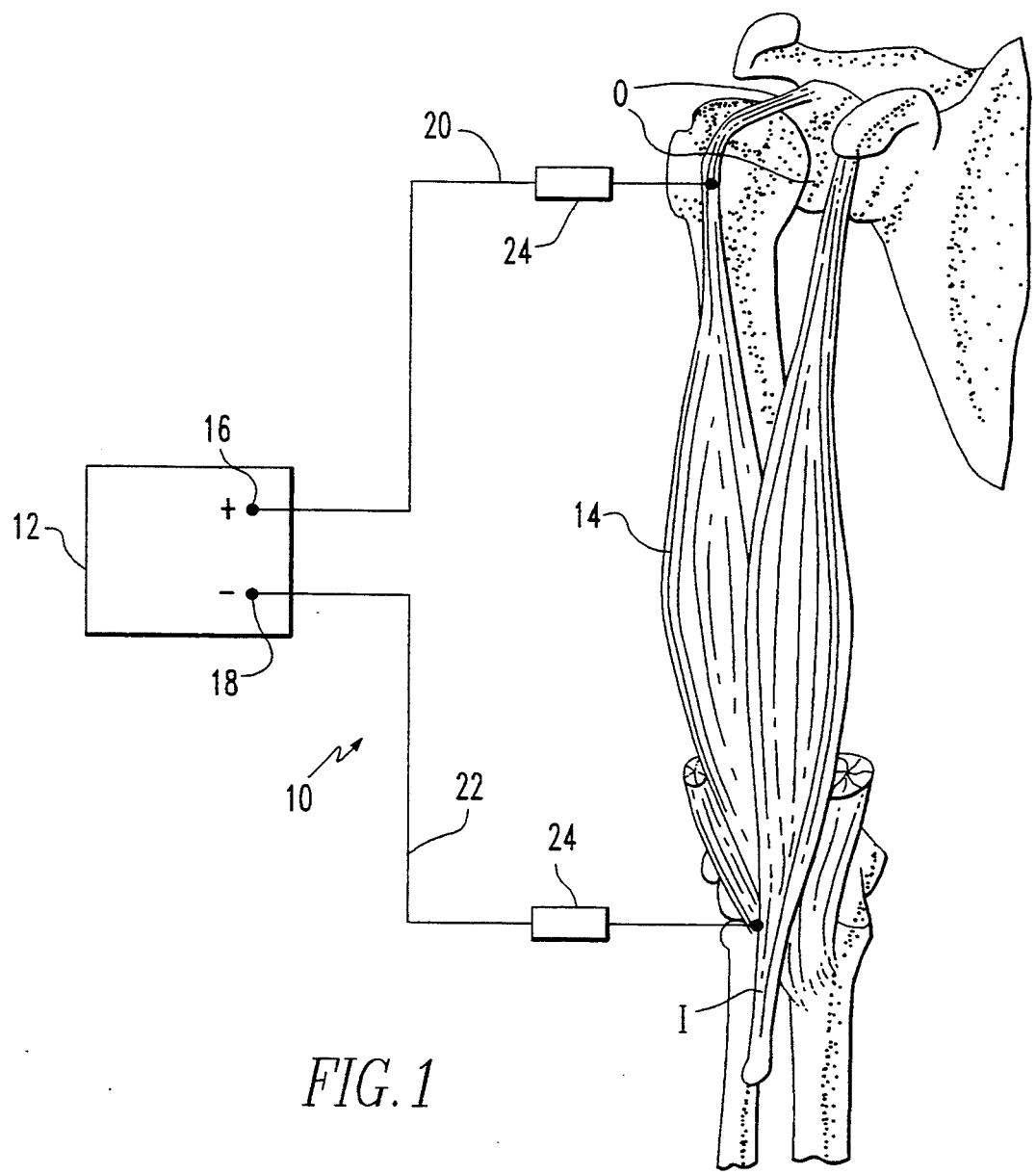

There is generally indicated at 10 in FIG. 1 my novel method being applied by use of an electrical stimulus generating apparatus 12 to a portion of the human anatomy 14, specifically the right biceps brachii muscle. This muscle is but one of many muscles which can be treated for pain according to my novel method, virtually any muscle tissue in the human anatomy being a candidate for such treatment.

In general, all muscles in the human body are characterized by a fibrous structure with strands or fibers extending longitudinally between end points of the muscle commonly designated as the origin end O and the insertion end I. The terms origin and insertion are to a degree arbitrary, generally signifying the point of attachment of the muscle to the relatively stationary skeletal structure (origin), and the point of attachment to the relatively movable skeletal structure (insertion). These terms thus are arbitrary in the sense that there is no absolute reckoning by which one portion of the skeletal structure may be regarded as stationary and another as movable. When movement occurs, there is merely relative movement between the skeletal structures in question. The terms origin and insertion, however, are not entirely arbitrary as there are structural differences in the muscle tissue, reckoned with regard to the origin and insertion ends. Consequently, the direction of current flow in the muscle can influence the efficacy of the treatment being applied. Accordingly, the apparatus 12 is provided with electrical connection points 16 and 18 to which are connected electrical leads 20 and 22, respectively. Connection points 16 and 18 are of opposite polarity, being positive and negative, respectively, as shown.

Each of leads 20 and 22 is connected to a probe 24 by which the electrical stimulus generated by apparatus 12 is applied, respectively, to the origin and insertion areas of muscle 14. The electrical current thus is passed longitudinally between the probes through the muscle tissue to provide the electrotherapy treatment according to my novel method as discussed hereinbelow.

My invention has been effective in resolving muscular pain regardless of the diagnosis, the causes of the pain, the age of the injury or the duration of the disease. Notably, it has been beneficial even where other modes of pain management have failed. When the source of pain is found to be muscular in nature, regardless of diagnosis, the method has been successful in achieving pain resolution for a very high percentage of patients treated. Exceptions include persons with secondary conditions relating to surgery or scar tissue. In the case of patients with chronic disease, the treatment method can be successful if utilized on an appropriate maintenance schedule. When applied appropriately, the method typically achieves pain relief on first treatment, with benefits noted in terms of decreased pain level, increased range of motion, or change in guarding.

Generally, the method can achieve cumulative effects. That is, one can rely on carryover from one treatment to the next in order to keep painful muscle contractions under control until the desired level of resolution and recovery are achieved.

I have found that my method generally provides best results when conducted in conjunction with various ancillary treatments. For example, stretching exercises and heat application directly after the electrotherapy treatment appears to enhance patient progress toward full recovery. Additionally, progress is enhanced when the patient follows a tissue detoxification program by eliminating certain foods from the diet such as caffeine, alcohol and sugar.

My method also has been effective in the treatment of pain associated with depression, anxiety and addictive behavior Such behavior is abated by my method in conjunction with abatement of muscle disfunction that is experienced as pain.

Initially, the patient's pain level or intensity is gauged using a T pain scale of 0 to 10 with 10 being most severe. This is done before treatment has begun and again after the treatment is finished. Use of the T pain scale is repeated in subsequent sessions to gauge progress. For patients lacking self awareness, the therapist must rely totally on objective indications including measurement of range of motion, intensity of muscle contraction, mobility and gait transition, stiffness, change in facial expression and decreased guarding.

The schedule of treatments depends upon the specifics of the condition being treated. When the patient has learned to compensate to a great degree as a spontaneous reaction to the pain, the entire body may be involved. The treatment thus would have to encompass the head and neck area, upper back area, lower back and buttocks area, and the legs and feet. The extent and complexity of such treatment, as called for in severe cases, typically may require six months of three two-hour sessions weekly.

For more moderate conditions, a less extensive regimen of treatment may suffice, for example four months of three two-hour sessions weekly. Mild conditions may require still less intense treatment, for example two months of three one-hour sessions weekly. New injuries or those that are one to six months old and exhibit a lesser number or magnitude of muscle involvement usually can be resolved in two to four weeks. With minimal muscle involvement, for example one to three muscles, the condition often can be resolved in one to three treatments within a two week period. In general, the duration, intensity, and other aspects of the treatment regimen must be determined by the therapist after analysis of the patient's condition.

Experience indicates that my method of electrotherapy alleviates pain symptoms in a descending, worst symptom first order, working toward the least bothersome symptoms. A characterization of worst to least bothersome pain symptoms may include: a. sharp shooting pain or radiating pain; b. burning pain; c. numbness; d. tingling; e. aching; f. soreness; g. tightness; and h. pulling.

Properly applied, my method has few deleterious side effects, although it should not be used on pregnant women and persons with pacemakers. As the method does detoxify tissue, a patient may experience nausea following the first several treatments. Drinking water after the treatment will stimulate flushing of toxins. These and other routine precautions are to be observed.

As noted above, one advantage of my electrotherapy method is that it effectively treats the perceived source of pain in patients regardless of diagnosis, thus allowing for prompt and cost effective pain resolution. Alleviation of pain can hasten recovery from most injuries and some illnesses. The pain reduction can also help a patient manage other related conditions or diseases more successfully. Of course, the patient's background information is very important and the report of the referring physician is essential, for among other reasons to confirm that proper diagnostic testing has been conducted and has ruled out pathology as the cause of the patient's pain. The information from the referring physician and from the patient interview forms the basis for the patient and the therapist to work together in identifying the source of the pain as perceived by the patient. Only then can the appropriate therapeutic regimen be developed and applied. Many conditions, injuries and diseases cause a patient to experience pain that can be resolved utilizing my method, and a number of sources of pain that respond to my method have been identified. For example, muscle contraction is a major cause of inpatient pain that responds to my method. Muscle contraction is characterized by a hardening of the muscle and attendant pain. When the contracted muscle is relaxed, the pain is relieved. This sort of condition relates to specific muscles. Muscle contractability is a more generalized or widespread condition relating to motor conditions affected by abnormal nerve conduction such as found in spinal cord injury, head injury, cerebral palsy and multiple sclerosis. Such muscle contractability involves a relatively large area of the body. For this reason, a different and more general sort of electrotherapy application method is necessary to produce pain attenuation.

My method can also effectively treat nerve involvement such as pain which occurs as a result of nerve compression by a contracted or tight muscle. One of the most common such conditions involves the piriformis muscle, located beneath the buttocks, as the inflicting muscle. Contracting or tightening of this muscle compresses the sciatic nerve. Treatment and isolation of the offending muscle with my method relaxes the muscle, relieves the nerve compression, and attenuates the attendant pain, including radiculopathy or radiating pain.

Although joint pain usually is associated with arthritis or other inflammatory illness, some joint pain can be directly related to muscle involvement. Examples would include the hamstring, sartorius and tensor fascia latae muscle group, constriction in either of which will cause knee pain. My electrotherapy method is effective for abating such pain. Further, a variation of my method is effective for treating joint pain related to inflammatory illness such as arthritis, although in this case the effects of the treatment are transitory and must be undertaken on a continuing maintenance basis.

My method also has been successfully applied for the treatment of circulation problems such as diabetic neuropathy, a condition characterized by a sense of cold, numbness and pain, and discoloration of the outer extremities of the affected limbs.

Still further, my novel method has been effective in treating soft tissue injuries such as sprains, contusions and tears, which can be notoriously slow in healing. Application of my method can decrease recovery time substantially, provided reinjury or progressive injury does not occur.

Other more specialized areas of application for my method include hormonal upsets or insufficiencies which can create emotional responses and fatigue in the patient, cognitive function which may be impaired or lost as a result of head injury or substance abuse, memory enhancement, concentration, information processing, and behavioral problems related to brain trauma (such as found in head injury or cerebral palsy), neuroses (such as anxiety and depression), and substance addiction. In most of such specialized applications, variations on my preferred method may be applied. Further, the relief provided in these cases may be only temporary or transitory, or require continuing maintenance. Of course, a consulting physician, psychiatrist, or other medical practitioner should deal simultaneously with any patient whose condition warrants such attention.

Although there are many devices for applying microcurrent therapy, my method includes preferably and predominately application with probes. Preferably the probes should be made from essentially pure silver only (99.99%), and the mode of conduction should be Q-tip and water. Probes are used in cases where muscle involvement is the primary issue. The probes permit improved isolation of origin and insertion points, more precise concentration of the electrical stimulus, deeper incursion of the current into the tissue, and a faster and greater response. Pads can be used in lieu of probes in treating conditions related to chronic disease processes where muscle involvement is not the primary issue such as motor spasticity, inflammation, diabetic neuropathy and sympathetic dystrophy. The pads also can be used in conjunction with the Naiad machine which spins the patient at a prescribed rate of rotation in a chamber which occludes all outside stimulation. This aspect of the method can be utilized to improve motor management in patients with conditions such as cerebral palsy, spinal cord injury, head injury and multiple sclerosis. Duration of the improvement in motor control may, by use of this variation of the method, be extended from several hours to several days.

In still another variation of my method, pads may be used in lieu of the probes to deliver the electrical stimulus in conjunction with massage of the patient's body using one pad covered with a conduction gel as the massage instrument. The other pad is maintained stationary adjacent to the most distant point of the injury pattern. In this way, lumps or nodules, if non-pathological in nature, can be broken down. One example of use of this variation is in the treatment of shingles.

In order for microcurrent therapy to be effective, the muscle being treated must be placed under active or passive stress. That is, it must be stretched in a flexed, extended, rotated, abducted or adducted manner. The function of the muscle determines which of these positions is the appropriate muscle stress adjunct to the electrotherapy treatment. In addition, the electrotherapy method requires that the body be placed in a position to best expose the muscle to be treated. There are potentially three different positions to be considered: relaxed, active stretch and passive stretch. A relaxed position refers to the patient being totally at ease during treatment. Active stretch refers to the patient placing the body or affected body portion in a state of stretch such as those mentioned above. The stretch is initiated by the patient if movement and palpation of the injured area can be tolerated. In passive stretch, the patient and therapist work together to create the desired level of intensity in a selected stretching movement to expose the muscle more prominently. Passive stretch appears generally to produce the best cumulative effect.

Patients may be treated by my method either attended or unattended. In general, new patients or those patients with severe trauma or chronic illness will be attended by a therapist throughout the entire duration of the treatment since most of the applicable treatment selection and problem solving must be done for such patients. Other patients may be treated unattended, the therapist being present only at intervals during the treatment session.

A very important aspect of my novel method is the direction of current flow. This applies regardless of the type of injury or disease being treated. There are six directional flows to be considered.

As noted above, muscle tissue fibers flow in a specific direction based on their points of origin and insertion. The origin and insertion points are defined somewhat arbitrarily, but are not necessarily interchangeable because the origin and insertion points also relate to muscle structure. When microcurrent applied according to my method flows against the muscle fiber, that is from insertion I to origin O with the negative probe placed at the insertion point, the muscle relaxes or loosens.

Of course, once the treatment location has been determined, the next decision for the therapist is whether the required muscle response is contraction or relaxation. The largest percentage of treatment applications will require muscle relaxation; however, exceptions may include such conditions as cerebral palsy, where a muscle may need to be tightened or contracted for greater control in ambulation. In such cases, the probes would be placed to produce an O-to-I current flow. That is, the negative polarity probe is placed at the muscle origin. This approach also has been used successfully with multiple sclerosis patients.

Thus, in applying the electrical stimulus to origin and insertion points of the patient's muscle, the negative and positive polarities of the probes must be properly positioned for proper current flow direction. For example, to induce current flow through a muscle from insertion to origin, the negative polarity probe would be regarded as the activator probe and, since current would flow from negative to positive probes, the negative or activator probe would be placed at the muscle insertion point.

When a stubborn muscle contraction is encountered, the method can be applied in conjunction with movement of one probe or the other along the respective origin or insertion muscle attachments. The predominate use of insertion-to-origin directional current flow would include sports injuries, lower and upper back injury, and neck injuries including whiplash and/or related injury such as TMJ.

Another dimension of current flow direction is the use of a distal to proximal approach, under which current flow moves from the distal or outer end of the limb toward the portion of the limb closer to the torso. In general, relatively distal locations correspond to muscle insertion points and relatively proximal locations correspond to muscle origin points. Accordingly, distal-to-proximal current flow corresponds in a great many instances to insertion-to-origin current flow, and many of the same use conditions and limitations apply, as discussed above.

For those muscles or muscle groups extending generally in a posterior to anterior direction, current flow from posterior to anterior obtains positive results whereas, by contrast, no reaction or result appears when current flow is applied in the opposite direction, or anterior to posterior. The posterior to anterior current flow direction also generally corresponds to insertion-to-origin current flow. Two important conditions that can be treated using a posterior-to-anterior current flow are painful menses, and headaches relating to allergies, TMJ, or tight neck muscles. In the case of headaches, involvement may include corresponding muscles in the neck and upper back. Palpation of these muscles can indicate the possibility of such involvement. It is to be noted that some types of headaches such as PMS headaches or those resulting from whiplash injury do not respond well to the posterior to anterior current flow technique. In the case of the PMS headaches, the reason appears to be a direct relation of such headaches to hormonal imbalance.

Long term painful conditions can give rise to related secondary conditions. For example, patients afflicted with chronic pain may become anxious and depressed, or dependent upon medication or liquor. The resulting addictive behavior, or the constant battle against emotional response that is not well managed by medication, can create severe muscle tension and attendant pain. In such instances, treating the muscles directly provides at best only temporary relief as the underlying cause is not being addressed. In some cases, the electrotherapy muscle treatment is preceded by transcranial electrotherapy, that is, with the electrical impulse directed from mastoid bone to mastoid bone to address the secondary conditions before treatment of the muscles.

For transcranial application of my electrotherapy method, which also corresponds to the described I-to-O current flow, the current is passed in the direction from the patient's dominant physical function side to the opposed side. One method of determining dominant physical function side is to observe dominant function visually. If the patient is righthanded, for example, as opposed to lefthanded, the electrical stimulus is passed transcranially from right to left. Another approach to determining dominant physical function side is to take voltage readings across the mastoid bones on the left and right sides of the head. The voltage reading is taken in two modes, one with the positive end negative probes applied to the left and right mastoid bones, respectively, and another with the probe locations interchanged. The higher voltage reading appears to be an indicator of dominant physical function side. For example, if the volt meter is set to indicate negative voltage, the location of the positive electrode when reading the higher voltage appears to indicate the dominant physical function side. This particular application of the electrical stimulus typically will be applied with pads rather than probes, and typically in conjunction with centrifugal force as developed by the Naiad spinning machine for enhanced benefit.

Transcranial electrotherapy may be applied in such cases as anxiety, panic attacks, depression, alcohol or other substance abuse, and for smoking and weight loss programs. Some applications of my method of electrotherapy involve local application wherein electrode pads are used to apply the electrical stimulus directly to the area of pain as opposed to directing it along the longitudinal aspect of the muscle fiber. This approach may be utilized in the treatment of soft tissue injuries such as tears, bruises and contusions. In still other conditions such as cerebral palsy, multiple sclerosis, and motor involvement with spinal cord or head injury, conduction of the electrical stimulus along a nerve pathway improves motor capability, apparently as a direct result of enhanced ability for nerve impulses to reach the respective voluntary muscles. In these cases also, a Naiad or similar spinning machine can be beneficial.

Another example of transverse direction, similar in some aspects to transcranial treatment, is treatment of the thymus gland which is located beneath the breast bone in the chest cavity. This treatment can be utilized to treat PMS or related headaches, if indeed an underlying cause of the headache is a hormonal imbalance. The electrical stimulus is applied transversely, passing from right to left, or left to right, from whichever side of the patient's body represents dominant physical function.

Of course, microcurrent therapy in general, and my novel method thereof in particular, require first that the muscles needing treatment be identified specifically. A work in two volumes by Jeannette Trevell, M.D. and David Simmons, M.D., titled Myofascial Pain and Disfunction, describes a pain pattern concept. The work illustrates which muscles would cause pain in specific situations and additionally provides considerable detail concerning symptoms that are observed in specific patterns of muscle involvement. The reader is referred to this work for a comprehensive discussion of various conditions resulting from muscle spasm or contraction and similar causes.

Figure 2:
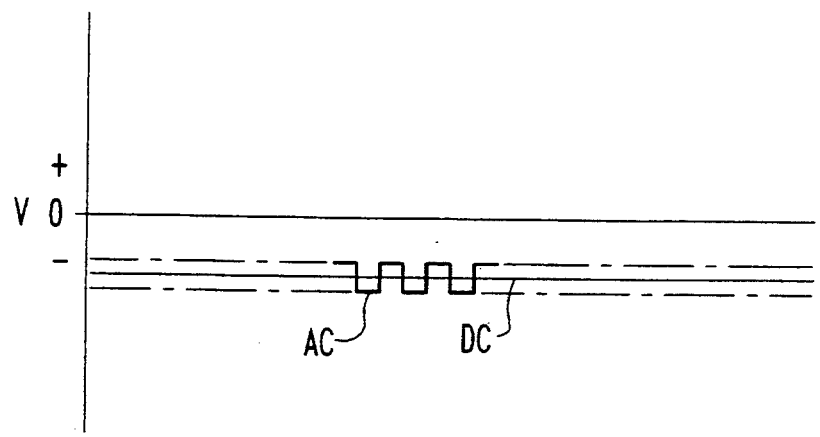

The technical aspects of my novel method of electrotherapy are of considerable importance to the method and must be followed quite closely. The preferred wave form of the electrical stimulus for my method is a square wave as shown in FIG. 2, although a sine wave (FIG. 3) may also be employed. Of course, the wave form relates only to the AC component of the superposed AC/DC electrical stimulus employed.

Figure 3:
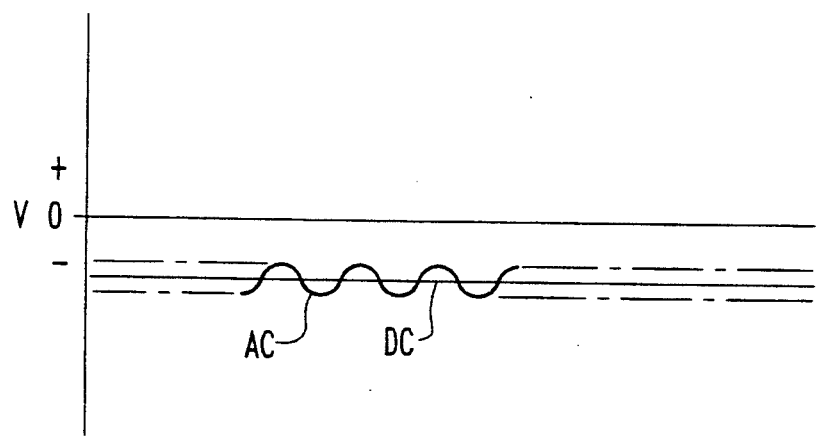
FIG. 3 illustrates an electrical stimulus voltage, polarity and wave form according to another preferred embodiment of my method.

More specifically, FIGS. 2 and 3 show the square and sine wave forms, respectively, as the variation of voltage over time. Each AC wave form is displaced from the $V_o$ base line into the negative voltage region by the superposed negative voltage DC component. In the description hereinbelow of electrical characteristics, the AC characteristics which vary with time, including voltage and current, are stated as half wave or base-to-peak values for the square wave signal. Of course, in a square wave, peak-to-peak values and RMS (root mean square) values will be same. For a sine wave AC component as in FIG. 3, the RMS values of current and voltage may be numerically different from certain values set forth hereinbelow for the preferred square wave AC component. It will be further appreciated that the AC component current wave form may lead or lag the AC component voltage wave form, depending upon the circuit impedance characteristic, including the electrical impedance characteristic of the muscle being treated.

Polarity refers to the charge carried by the wave form, either positive, negative or neutral. Although a number of variables can influence the choice of polarities, including skin resistance, health of tissue, and sensitivity to the electro-magnetic field among others, generally the method calls for negative AC/DC polarity (FIGS. 2 and 3) as the polarity mode which offers maximum benefit in terms of greatest impact on the tissue being treated and acceptance by the patient. Use of negative AC/DC polarity appears to result in greater carry-over of positive effect from one treatment to the next.

As noted, my preferred polarity is that of the superposed AC (alternating current) and DC (direct current) electrical stimulus components. By current, I refer to the flow of electrons, measured in amperage, that is utilized to excite or trigger a response. I have found that very small magnitudes of amperage can trigger a beneficial chemical response in the tissue being treated. By contrast, the relatively high current values of conventional electrotherapy can increase friction and reduce patient safety and comfort. According to my method, the preferred value of current amperage is 20 microamps and the preferred range is 10 to 100 microamps.

The method further relies on proper choice of frequency for the electrical stimulus. Frequency is designated in hertz, the unit specifying the vibratory state of the current wave in cycles per second. Low frequencies can have a greater impact due to greater muscle penetration. A low frequency also appears to maximize the mobilization of accumulated toxins such as lactic acid and calcium deposits for excretion thereof. Toxin removal is an important aspect of my electrotherapy treatment. My preferred microcurrent frequency for both muscle impact or penetration and toxin mobilization and transport is 15 hertz and the preferred range is 0.01 to 150 hertz. For stress or cognitive conditions my preferred microcurrent frequency is 3 hertz, although more generally a frequency in the range of 4 to 7 hertz may be employed.

Voltage is a further parameter of electrical current flow and refers to the electromotive force behind the current flow. For my method the preferred voltage values are $-3.5$ volts for the DC component, and $-1.5$ volts for the AC component. My preferred voltage ranges are $-0.01$ to $-6.5$ volts for the DC component, and $-0.01$ to $-6.5$ volts for the AC component. It will be noted that the voltage value of the AC component in both FIGS. 2 and 3 is selected, with regard to the value of the DC voltage component, such that the instantaneous AC voltage value at any point in the wave form is essentially always a non-positive voltage value.

In order to carry out my method as above described, an electrical stimulus generator 12 capable of generating an electrical output with the characteristics above described is to be utilized. I am unaware of any commercially available apparatus designed specifically for electrotherapy applications that can generate such output characteristics; however, the electrical components necessary to produce the electrical output characteristics I have described are well known to those versed in the art, as would be the manner of constructing an apparatus to provide those outputs. For example, a conventional function generator can produce the desired output characteristics. Although the apparatus I use to provide the outputs for microcurrent therapy in accordance with the electrical characteristics specified hereinabove is one I had custom made by a teacher and practitioner of electrical engineering, I regard that specific apparatus as equivalent to any alternative apparatus design that would provide the described output characteristics. For purposes of convenience and portability, the apparatus preferably uses batteries for a power source, for example standard alkaline D cells in sufficient quantity or NiCAD rechargeable batteries, depending upon the intentions and requirements of the user. I have been advised that apparatus to provide the described output characteristics is well enough known and understood in the art that a junior or senior level electrical engineering student should be able to design such an apparatus without difficulty.

Figure 4:
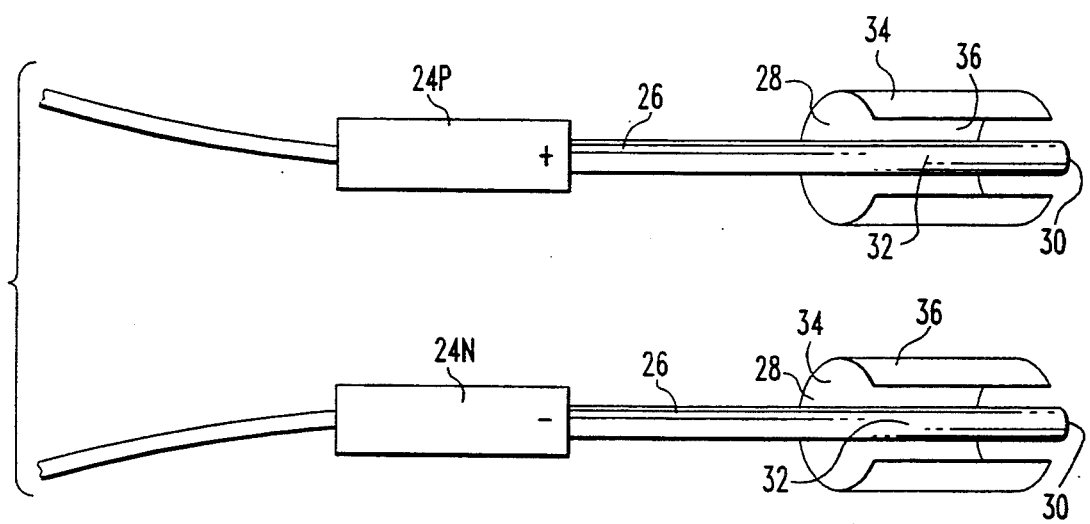
FIG. 4 is a detailed view of the proves of FIG. 1 showing an alternative embodiment of the invention.

In n alternative embodiment of the invention, magnetized tape is utilized in conjunction with the probes, pads or other microcurrent application instrument. For example, referring to FIG. 4 the probes 24 have electrical polarities designated as positive probe 24P and negative probe 24N. Each probe includes an elongated conductive portion 26 which, as indicated hereinabove, may preferably be of pure silver. A magnetized tape strip 28 is wrapped around each conducting portion 26 and retained by any suitable means in engagement with the peripheral surface 32 of the probe adjacent the free or contact end 30 of each conducting portion 26. In FIG. 4 the magnetized tape 28 is shown encircling the respective conducting portions 26 but not in contact with them so that the opposed surfaces of the magnetized tape are clearly shown. Tape 28 thus is a thin-section expanse of flexible magnetized material having opposite magnetic polarities on its opposed flat sides. In practice, magnetized tape 28 passes about the peripheral surface 32 of each conducting portion 26 in engagement therewith.

Magnetized tape 28 is classified as a "straight through" tape, meaning that the opposed flat sides of the tape are of opposed magnetic polarity. Such magnetized tape is commercially available. I have acquired such tape from Dexter Magnetic Materials, Inc. of Toledo, Ohio. One particular tape product of this supplier which I have successfully used in the manner specified is product No. 1016, Plastiform TM brand flexible magnetized tape having a thickness of 3/32 in. (0.093 in.) and magnetized "straight through" with a density of 18 poles/inch.

As specified, the magnetic tape 28 has opposed flat sides which are of opposite magnetic polarity. For example, a first flat side thereof 34 is of positive (i.e. South) magnetic polarity and the opposed side 36 thereof is of negative (i.e. North) magnetic polarity. A length of the magnetized tape 28 is applied to surface 32 of negative probe 24N, with the positive polarity surface 34 thereof in contact with probe surface 32. For the positive probe 24P, the magnetized tape 28 applied thereto has the negative polarity side 36 in contact with the peripheral surface 32 of the probe. The specified polarity relationship for the magnetized tape on the respective probes is required in order to provide effective treatment. Failure to place the tape properly may result in a rebound effect characterized by the treated muscle tightening or contracting further rather than relaxing. This will be the opposite of the effect desired.

The same sort of magnetized tape placement can be utilized when pads are used in lieu of probes for the described electrotherapy. That is, the magnetized tape is placed on the pads with the negative polarity tape side or surface engaging the positive pad and the positive polarity tape side or surface engaging the negative pad. Thus, the negative pad contacts the positive polarity side of the magnetic tape which, through a conducting material has its negative polarity side contacting the patient's skin. For the positive pad, the negative polarity side of the tape contacts the pad and, through a suitable conducting material, the positive polarity side thereof contacts the patient's skin.

The purpose of using the magnetized tape as described is that I have discovered an enhanced or intensified magnetic field can be beneficial in the electrotherapy treatment of various medical conditions when applied simultaneously with application of an electrical stimulus adjacent insertion and origin locations as described hereinabove. Differences in specific magnetic field configurations including positive, negative, alternating and direct, can have differing effects in treatment of muscle pain or for patients with decreased muscular strength such as is observed in motor neuron diseases. I believe other differences in treatment efficacy will appear as a result of the use of varying frequencies for alternating magnetic fields, reflection and concentration of such fields as by parabolic reflectors, and finally the combination of differing magnetic field configurations as well as the combining of such differing magnetic fields with other therapeutic stimuli such as light, sound, microcurrent and physical spinning of the patient such as above described.

Among the described variations, using reflected and/or concentrated magnetic fields appears to offer greater impact and effect for electrotherapy treatment in a shorter time span than would otherwise be required. Utilizing reflected magnetic fields also appears to offer the benefit of greater carryover from one treatment to the next.

The origin-insertion relationship described hereinabove for application of the positive and negative probes or pads, as well as other aspects of the invention, also apply for probes or pads with added magnetized tape, as described.

According to the description hereinabove, I have invented a novel and improved electrotherapy method which relies on specified values of the parameters which define the electrical stimulus, including polarity, frequency, current level, voltage, wave form and current flow direction. I have found the use of my method in accordance with the specified ranges or values of these parameters results in considerable improvement in patient response and benefit over prior modes of electrotherapy.

Of course, I have contemplated various alternative and modified embodiments of my invention, and certainly such would also occur to others versed in this art once they were apprised of my invention. Accordingly, I intend that the invention should be construed broadly and limited only by the scope of the claims appended hereto.

I claim:

1. An electrotherapy treatment method for influencing the relative state of contraction of selected muscles of a patient's anatomy comprising the steps of:
   providing an electrical stimulus comprised of an electrical current of a continuously negative voltage and having superposed AC and DC components and the characteristics of negative polarity and a current value in the range of about 10 microamperes to about 100 microamperes, with said AC component having the further characteristic of a frequency in the range of about 0.01 hertz to about 150 hertz, and;
   applying said electrical stimulus to such a patient's body at locations corresponding to insertion and origin portions of such muscles in a manner to pass said electrical current through such muscles from said insertion portion toward said origin portion thereof.

2. The method as set forth in claim 1 including the additional step of applying said electrical current simultaneously with rotation of the patient with respect to the earth reckoned as a stationary frame of reference.

3. The method as set forth in claim 2 wherein said rotation of the patient is rotation of the sort achieved by use of a Naiad apparatus.

4. The method as set forth in claim 1 wherein said applying step includes application of said electrical current to such a patient's body with probes.

5. The method as set forth in claim 4 additionally including application of an enhanced magnetic field at said locations corresponding to said insertion and said origin portions by positioning a magnetized medium adjacent said probes.

6. The method as set forth in claim 5 wherein said positioning a magnetized medium includes wrapping a portion of each of said probes with flexible magnetized tape having opposed sides of opposite magnetic polarity, respectively.

7. The method as set forth in claim 6 wherein said probes have opposite electrical polarities, respectively, and said positioning a magnetized medium includes wrapping a portion of each said probe with said magnetized tape in a manner that the side of said magnetized tape engaging said probes is of a magnetic polarity opposite the electrical polarity of said probes, respectively.

8. The method as set forth in claim 1 wherein said frequency is approximately 15 hertz.

9. The method as set forth in claim 1 wherein said current is approximately 20 microamperes.

10. The method as set forth in claim 1 wherein said negative voltage is in the range of about $-0.01$ volts to about $-6.5$ volts.

11. The method as set forth in claim 10 wherein said negative voltage of said DC component is approximately $-3.5$ volts.

12. The method as set forth in claim 11 wherein said negative voltage includes a voltage variation of approximately 1.5 volts alternately in the plus and minus directions from said negative voltage of said DC component.

13. The method as set forth in claim 12 wherein said AC component includes the further characteristic of a generally square wave form.

14. The method as set forth in claim 1 wherein said AC component includes the further characteristic of a generally square wave form.

15. The method as set forth in claim 1 wherein said AC component includes the further characteristic of a generally sinusoidal wave form.

16. The method as set forth in claim 1 wherein said applying step is preceded by application of said electrical current to transversely spaced locations on such a patient's body in a manner to pass said electrical current transversely in such a patient's body from the transverse side of dominant physical function toward the opposed transverse side thereof.

17. The method as set forth in claim 1 additionally including application of an enhanced magnetic field to such a patient's body at locations corresponding to said insertion and origin portions simultaneously with application of said electrical stimulus at said locations corresponding to said insertion and origin portions.

18. An electrotherapy treatment method for the alleviation of pain by influencing the relative state of contraction of selected muscles of a patient's anatomy comprising the steps of:
providing an electrical stimulus comprised of an electrical current of a continuously negative voltage and having superposed AC and DC components and the characteristics of negative polarity and a current value in the range of about 10 microamperes to about 100 microamperes, with said AC component having the further characteristic of a frequency in the range of about 0.01 hertz to about 150 hertz, and;
applying said electrical stimulus to such a patient's body at locations corresponding to insertion and origin portions of such muscles in a manner to pass said electrical current through such muscles from said insertion portion toward said origin portion thereof.

19. The method as set forth in claim 18 additionally including application of an enhanced magnetic field to such a patient's body at locations corresponding to said insertion and origin portions simultaneously with application of said electrical stimulus at said locations corresponding to said insertion and origin portions.

20. In a treatment for influencing the relative state of contraction of selected muscles of a patient's anatomy, an electrotherapy method comprising the steps of:
applying an electrical stimulus to the body of such a patient, said electrical stimulus being a continuously negative voltage AC wave.

21. The method as set forth in claim 20 wherein said negative voltage is in the range of about $-0.01$ volts to about $-6.5$ volts.

22. The method as set forth in claim 21 wherein said negative voltage varies from a baseline voltage in said range alternately in positive and negative directions by about 1.5 volts.

23. The method as set forth in claim 20 wherein said electrical stimulus includes the characteristic of a current value in the range of about 10 microamperes to about 100 microamperes.

24. The method as set forth in claim 20 wherein said electrical stimulus includes the further characteristic of a frequency in the range of about 0.01 hertz to about 150 hertz.

25. The method as set forth in claim 20 wherein said AC wave form is a generally square wave form.

26. The method as set forth in claim 20 additionally including application of an enhanced magnetic field to such a patient's body simultaneously with application of said electrical stimulus thereto.

* * * * *